(12) United States Patent
Lee et al.

(10) Patent No.: US 6,564,648 B2
(45) Date of Patent: May 20, 2003

(54) METHOD AND APPARATUS FOR INSPECTING SOLDER BALLS ON BALL GRID ARRAY PACKAGE

(75) Inventors: Lan-Song Lee, Taichung (TW); Hsing-An Hsu, Taichung (TW)

(73) Assignee: Siliconware Precision Industries Co., Ltd. (TW)

( * ) Notice: Subject to any disclaimer, the term of this patent is extended or adjusted under 35 U.S.C. 154(b) by 172 days.

(21) Appl. No.: 09/800,359

(22) Filed: Mar. 5, 2001

(65) Prior Publication Data

US 2002/0121149 A1 Sep. 5, 2002

(51) Int. Cl.[7] .................................................. G01N 3/24
(52) U.S. Cl. ........................................... 73/842; 73/845
(58) Field of Search ........................ 73/842, 843, 845, 73/865.9; 198/339.1

(56) References Cited

U.S. PATENT DOCUMENTS

| 3,429,840 | A | * | 2/1969 | Miller ........................... 29/840 |
| 3,611,795 | A | * | 10/1971 | Goldmenn et al. ....... 73/843 X |
| 5,095,683 | A | * | 3/1992 | Holiday .................. 73/865.9 X |
| 6,035,731 | A | * | 3/2000 | Langmeck et al. ......... 73/865.9 |

FOREIGN PATENT DOCUMENTS

JP          6252220    *  9/1996  ............. G01N/3/24

* cited by examiner

*Primary Examiner*—Thomas P. Noland
(74) *Attorney, Agent, or Firm*—Peter F. Corless; Steven M. Jensen; Edwards & Angell, LLP

(57) ABSTRACT

A method and art apparatus are proposed for inspecting solder balls on a BGA (Ball Grid Array) package, which are capable of rejecting defectively-bonded solder balls while allowing properly-bonded ones to pass therethrough. The proposed method and apparatus are characterized by the use of a rotatable disk having a plurality of flaps arranged at equal angular intervals along the perimeter thereof, and which is capable of being rotated in steps if a force greater than a preset threshold torque is being applied tangentially to any one of the flaps. The threshold torque is set to be equal to or less than the shear-resistant strength of a properly-bonded solder ball but greater than the shear-resistant strength of a defectively-bonded one. During an inspection procedure, the BGA package is moved toward the rotatable disk to allow each solder ball to push against one of the flaps on the rotatable disk. If a solder ball is a properly-bonded one, it would be capable of pushing open the flap and therefore passing through the inspection procedure; otherwise, for a defectively-bonded solder ball, it would be rejected and broken apart from the BGA package by the flap. Therefore, as the entire BGA package has undergone the inspection procedure trough the rotatable disk, all properly-bonded solder balls would remain in position over the BGA package, while all defectively-bonded ones would be removed.

8 Claims, 3 Drawing Sheets

METHOD AND APPARATUS FOR INSPECTING SOLDER BALLS ON BALL GRID ARRAY PACKAGE

BACKGROUND OF THE INVENTION

1. Field of the Invention

This invention relates to semiconductor packaging technology, and more particularly, to a method and an apparatus for inspecting solder balls on a BGA (Ball Grid Array) package, which are capable of rejecting defectively-bonded solder balls while allowing properly-bonded ones to pass therethrough.

2. Description of Related Art

BGA (Ball Grid Array) is an advanced type of semiconductor packaging technology which is characterized in the use of a substrate whose front side is mounted with a semiconductor chip and whose back side is implanted with a grid array of solder balls. During SMT (Surface Mount Technology) processes, the BGA package can be mechanically bonded and electrically coupled to an external printed circuit board (PCB) by means of these solder balls.

Fundamentally, a solder ball is said to be properly bonded if the bonding strength between the solder ball and its solder-ball pad is adequate enough to withstand a certain magnitude of shear. For example, for a solder ball of 0.75 mm in diameter, it should be at least able to withstand a ball shear of 1 kg; otherwise, it would be regarded as defectively bonded. A defectively-bonded solder ball would be easily broken apart from its solder-ball pad during transportation and handling. By conventional BGA fabrication, however, solder balls may often be defectively bonded due to the solder-ball pads being oxidized or contaminated by chemicals during the fabrication processes. This problem is illustratively depicted in the following with reference to FIGS. 1A–1C.

FIG. 1A shows the structure of a typical BGA package 10. As shown, this BGA package 10 is constructed on a substrate 11 whose front side is mounted with a semiconductor chip 12 and whose back side is formed with an array of solder-ball pads 13 masked by a solder mask 14. The solder-ball pads 13 are typically plated with gold (Au) to increase the solder-wettability thereof.

During a ball-implantation process, a grid array of solder balls 15 are attached to the respective solder-bail pads 13 and then reflowed to allow them to be wetted to the same. This allows the solder balls 15 to be mechanically and electrically bonded to the respective solder-ball pads 13.

As illustrated in FIG. 1B, during earlier BGA fabrication processes, however, the solder-ball pads 13 may be degraded in solder-wettability due to the existence of some wettability-degrading substances 16 over the surface thereof, which would degrade the solder-wettability of the solder-ball pads 13. The wettability-degrading substances 16 include, for example, the oxidation of the Au-plated surface of the solder-ball pads 13 and the remnant mask material and etchant that are left over the solder-ball pads 13 after the solder mask 14 is fabricated through a selective etching process. Since these wettability-degrading substances 16 are electrically insulative and non-wettable to solder, they would considerably degrade the solder-wettability of to solder-ball pads 13.

As further illustrated in FIG. 1C, if one of the solder-ball pads 13 is degraded in solder-wettability to a certain degree, it would undesirably cause the subsequently implanted solder ball 15 thereon to be defectively bonded; and consequently, during transportation or handling, the defectively-bonded solder ball 15 can be easily broken apart from its solder-ball pad 13. Even if the defectively-bonded solder ball 15 remains in position during transportation and handling, the wettability-degrading substances 16 would nevertheless cause an unreliable electrical coupling between the solder ball 15 and the solder-ball pad 13, making the finished BGA package 10 unreliable to use.

There exists therefore a need for a method and apparatus for use in quality control of implanted solder balls on a BGA package and which is capable of rejecting defectively-bonded solder balls while allowing properly-bonded ones to pass therethrough.

SUMMARY OF THE INVENTION

It is therefore an objective of this invention to provide a method and an apparatus for inspecting solder balls on a BGA package, which are capable of rejecting defectively-bonded solder balls while allowing properly-bonded ones to pass therethrough.

In accordance With the foregoing and other objectives, the invention proposes a novel method and apparatus for inspecting solder balls on BGA package.

In terms of method, the invention comprises the following steps (1) providing a rotatable disk having at least one flap on the perimeter thereof, the rotatable disk being capable of being rotated if a tangential force applied to the flap is greater than a predefined threshold torque set to be equal to or less than the shear-resistant strength of a properly-bonded solder bail but greater than the shear-resistant strength of a defectively-bonded one; (2) providing a conveyance path for conveying the BGA package; and (3) positioning the rotatable disk above the conveyance path, with the flap thereon being suspended above the conveyance path to allow the solder ball on the BGA package to push tangentially against the flap; wherein the solder ball would be capable of pushing open the flap if it is a properly-bonded one and would be rejected and broken apart from the BGA package by the flap if it is a defectively-bonded one.

In terms of apparatus, the invention comprises: (a) a conveyance belt for conveying the BGA package; (b) a rotatable disk having at least one flap on the perimeter thereof; the rotatable disk being capable of being rotated if a tangential force applied to the flap, is greater than a predefined threshold torque set to be equal to or less than the shear-resistant strength of a properly-bonded solder ball but greater than the shear-resistant strength of a defectively-bonded one; and the rotatable disk being fixed above the conveyance belt with the flap being suspended above the conveyance path to allow the solder ball on the BGA package to push tangentially against the flap; wherein the solder ball would be capable of pushing open the flap if it is a properly-bonded one and would be rejected and broken apart from the BGA package by the flap if it is a defectively-bonded one.

By the method and apparatus of the invention, as a BGA package has undergone the inspection procedure through the rotatable disk, all the properly-bonded ones of the solder balls on the BGA package would remain in position over the BGA package, while all the defectively-bonded ones would be removed.

BRIEF DESCRIPTION OF DRAWINGS

The invention can be more fully understood by reading the following detailed description of the preferred embodiments, with reference made to the accompanying drawings, wherein.

DETAILED DESCRIPTION OF PREFERRED EMBODIMENTS

A preferred embodiment of the method and apparatus according to the invention for inspecting solder balls on a BGA package is disclosed in full details in the following with reference to FIGS. 2A–2D.

Figure 1A:
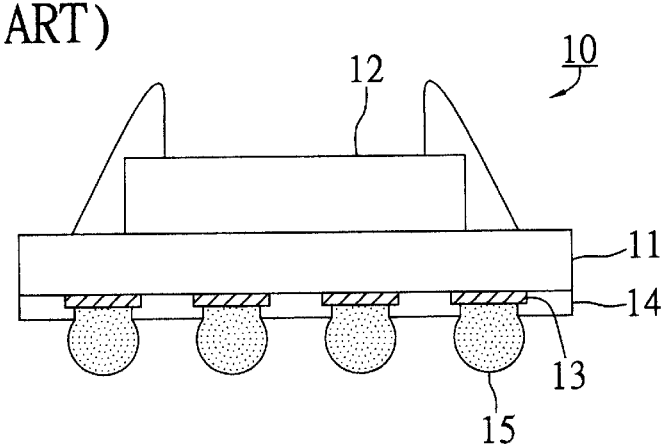
FIGS. 1A–1C (PRIOR ART) are schematic diagrams used to depict a conventional BGA package structure and the cause of defectively-bonded solder balls on the BGA package.
Figure 1B:
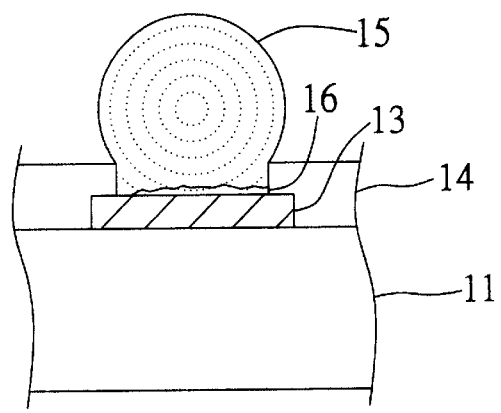
Figure 1C:
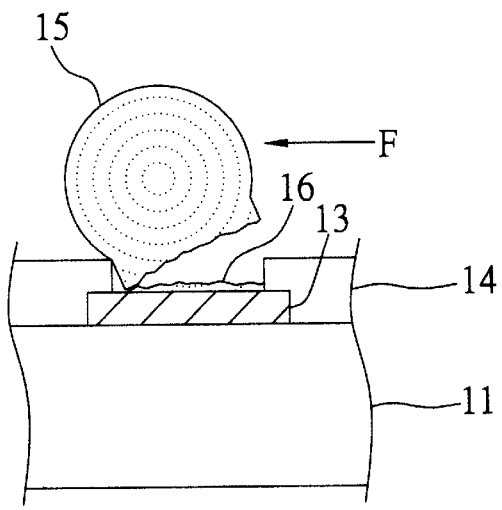
Figure 2A:
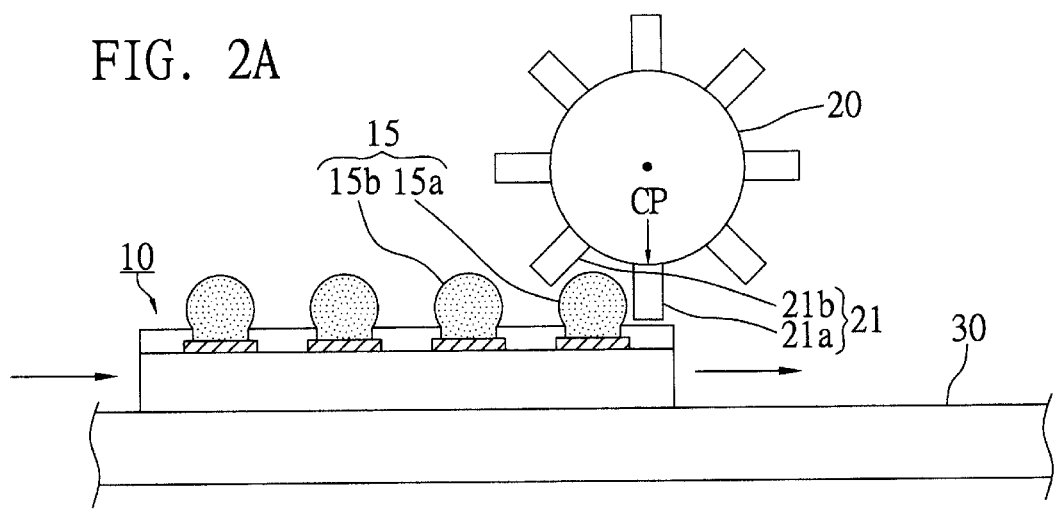
FIGS. 2A–2D are schematic diagrams used to depict the method and apparatus of the invention for inspecting solder balls on a BGA package.

Referring first to FIG. 2A, the method and apparatus of the invention are used for inspecting a BGA package 10 to check whether the grid array of solder balls 15 implanted thereon are properly-bonded or defectively-bonded. In the example of FIGS. 2A–2D, assume that the first solder ball 15a is a properly-bonded one, while the second solder ball 15b is a defectively-bonded one.

The method and apparatus of the invention include the use of a rotatable disk 20 having a ring array of flaps 21 (including a first flap 21a and a second flap 21b) arranged at equal angular intervals along the perimeter thereof, and which is capable of being rotated in steps if a force greater than a preset threshold torque is being applied tangentially to any one of the flaps 21. By the invention, the threshold torque of the rotatable disk 20 is set to be equal to or less than the shear-resistant strength of a properly-bonded solder ball but greater than the shear-resistant strength of a defectively-bonded one. The rotational steps are set to be equal to the angular intervals of the flaps 21, so that when the rotatable disk 20 is rotated once by pushing forcefully against the first flap 21a, it will set the next flap 21b to the cheek point CP above a conveyance belt 30.

The flaps 21 on the rotatable disk 20 are preferably made of a pliant material having a rigidity less than the solder balls 15 on the BGA package 10, such as a plastic material or a Teflon (polytetrafluoroethylene) material, so that the flaps 21 would not cause surface damage to the solder balls 15 when the solder balls 15 undergo the inspection procedure through the rotatable disk 20.

The rotatable disk 20 is fixedly mounted above the conveyance belt 30 used for conveying the BGA package 10 through the inspection procedure. Initially, the first flap 21a is set vertically suspended above the conveyance belt 30. When the BGA package 10 is being moved along the conveyance belt 30, it allows the first solder ball 15a in the ball grid army 15 to push against the first flaps 21a.

Figure 2B:
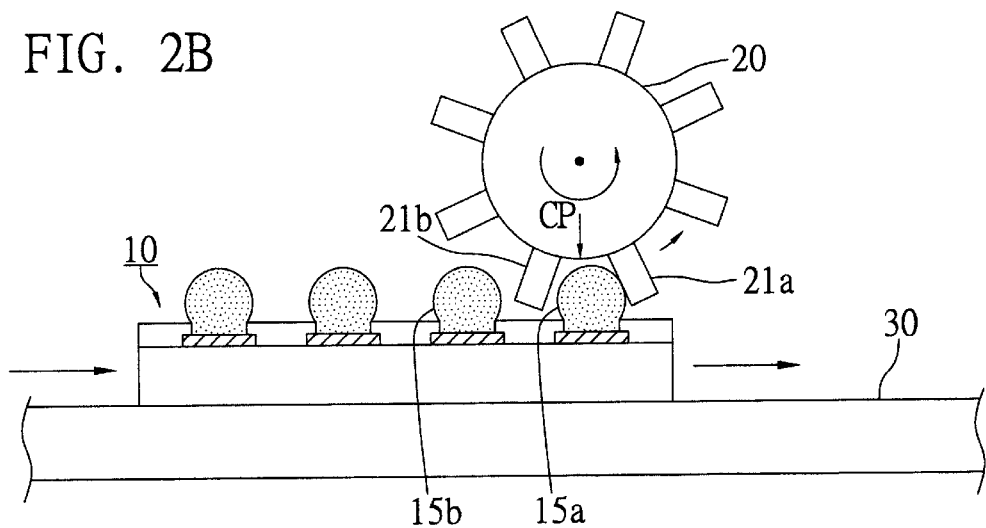

Referring further to FIG. 2B, as the BGA package 10 is being moved along the conveyance belt 30, it will allow the first solder ball 15a (which is a properly-bonded one) to push against die flap 21a. Since the first solder ball 15a is a properly-bonded one, it would have a shear-resistant strength greater than the threshold torque of the rotatable disk 20, thereby being capable of pushing open the first flap 21a and passing through the check point CP.

Figure 2C:
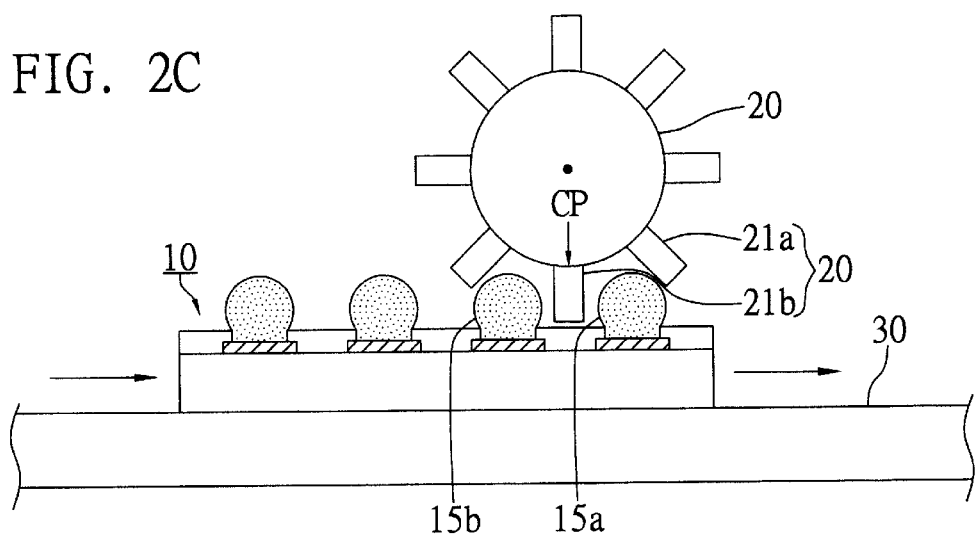

Referring next to FIG. 2C, as the properly-bonded solder ball 15a passes through the first flap 21a, the rotatable disk 20 is rotated by one step and thereby sets the second flap 21b vertically suspended above the conveyance belt 30 for the inspection of the second solder ball 15b (which is a defectively-bonded one).

Figure 2D:
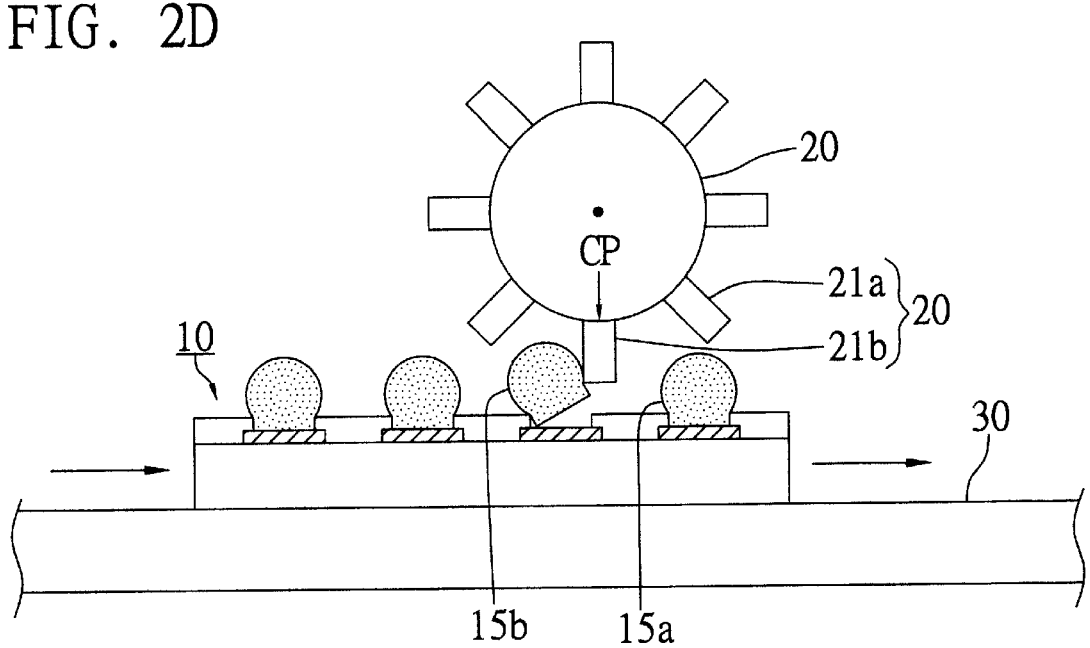

Referring next to FIG. 2D, since the second solder ball 15b is a defectively-bonded one, its shear-resistant strength would be less than the threshold torque of the rotatable disk 20 and therefore incapable of pushing open the second flap 21b. As a result, since the conveyance belt 30 continues to move the BGA package 10, it will force the defectively-bonded solder ball 15b to be broken apart from the BGA package 10 by the second flap 21b, thereby being rejected as a defectively-bonded solder ball.

Therefore, as the entire BGA package 10 has undergone the inspection procedure through the rotatable disk 20, all the properly bonded ones of the solder balls 15 would remain in position over the BGA package 10, while all the defectively-bonded ones would be removed and new ones can be re-implanted.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A method for inspecting a solder ball on a BGA package, comprising the steps of:
   (1) providing a rotatable disk having at least one flap on a perimeter thereof, the rotatable disk being capable of being rotated if a tangential force applied to the flap is greater than a predefined threshold torque set to be equal to or less than a shear-resistant strength of a properly-bonded solder ball but greater than the shear-resistant strength of a defectively-bonded one;
   (2) providing a conveyance path for conveying the BGA package; and
   (3) positioning the rotatable disk above the conveyance path, with the flap thereon being suspended above the conveyance path to allow the solder ball on the BGA package to push tangentially against the flap;
   wherein the solder ball would be capable of pushing open the flap if it is a properly-bonded one and would be rejected and broken apart from the BGA package by the flap if it is a defectively-bonded one.

2. The method of claim 1, wherein in said step (1), the flap on the rotatable disk is made of a pliant material having a rigidity less than the solder ball on the BGA package.

3. The method of claim 2, wherein the pliant material is a plastic material.

4. The method of claim 2, wherein the pliant material is polytetrafluoroethylene.

5. An apparatus for inspecting a solder ball on a BGA package, which comprises:
   (a) a conveyance belt for conveying the BGA package;
   (b) a rotatable disk having at least one flap on a perimeter thereof,
   the rotatable disk being capable of being rotated if a tangential force applied to the flap is greater than a predefined threshold torque set to be equal to or less than a shear-resistant strength of a properly bonded solder ball but greater than the shear-resistant strength of a defectively-bonded one; and the rotatable disk being fixed above the conveyance belt with the flap being suspended above the conveyance path to allow the solder ball on the BGA package to push tangentially against the flap;

wherein the solder ball would be capable of pushing open the hap if it is a properly-bonded one and would be rejected and broken apart from the BGA package by the flap if it is a defectively-bonded one.

6. The apparatus of claim 5, wherein the flap on the rotatable disk is made of a pliant material having a rigidity less than the solder ball on the BGA package.

7. The apparatus of claim 6, wherein the pliant material is a plastic material.

8. The apparatus of claim 6, wherein the pliant material is polytetrafluoroethylene.

* * * * *